(12) United States Patent
Velpandian (10) Patent No.: US 11,701,301 B2
(45) Date of Patent: Jul. 18, 2023

(54) DEVICE, METHOD AND KIT FOR THE RECONSTITUTION OF A SOLID OR SEMI SOLID PHARMACEUTICAL COMPOSITION

(71) Applicant: ALL INDIA INSTITUTE OF MEDICAL SCIENCES (AIIMS), New Delhi (IN)

(72) Inventor: Thirumurthy Velpandian, New Delhi (IN)

(73) Assignee: ALL INDIA INSTITUTE OF MEDICAL SCIENCES (AIIMS), New Delhi (IN)

( * ) Notice: Subject to any disclaimer, the term of this patent is extended or adjusted under 35 U.S.C. 154(b) by 403 days.

(21) Appl. No.: 16/491,196

(22) PCT Filed: Mar. 5, 2018

(86) PCT No.: PCT/IN2018/050115
§ 371 (c)(1),
(2) Date: Sep. 5, 2019

(87) PCT Pub. No.: WO2018/163201
PCT Pub. Date: Sep. 12, 2018

(65) Prior Publication Data
US 2020/0030188 A1 Jan. 30, 2020

(30) Foreign Application Priority Data
Mar. 6, 2017 (IN) .............................. 201711007747

(51) Int. Cl.
*A61J 1/20* (2006.01)
*A61J 1/14* (2023.01)
*A61F 9/00* (2006.01)

(52) U.S. Cl.
CPC ............ *A61J 1/2089* (2013.01); *A61J 1/1468* (2015.05); *A61J 1/2013* (2015.05); *A61J 1/2048* (2015.05); *A61F 9/0008* (2013.01)

(58) Field of Classification Search
CPC ....... A61J 1/2089; A61J 1/1468; A61J 1/2013; A61J 1/2048; A61J 1/2055; A61F 9/0008
(Continued)

(56) References Cited

U.S. PATENT DOCUMENTS 3,206,080 A * 9/1965 Scislowicz ............ A61J 1/2089
222/207
3,872,867 A * 3/1975 Killinger ............... A61J 1/2089
206/219
(Continued)

FOREIGN PATENT DOCUMENTS

WO      99/27886 A1    6/1999
WO      01/68166 A1    9/2001
(Continued)

OTHER PUBLICATIONS

Jun. 29, 2018 International Search Report issued in International Patent Application No. PCT/IN2018/050115.
(Continued)

*Primary Examiner* — Erich G Herbermann
*Assistant Examiner* — Seth Han
(74) *Attorney, Agent, or Firm* — Oliff PLC (57) ABSTRACT

A novel device, method and kit for reconstitution of a solid or semi-solid pharmaceutical composition by a negative pressure differential includes (i) a first adapter with a first connector, a first peripheral wall wherein the first adapter is coupled to the first vial by means of a first connector; (ii) a second adapter with a second connector, a second peripheral wall wherein the second adapter is coupled to the second vial by means of a second connector; (iii) a transfer port wherein
(Continued)

the transfer port includes a first end ending in first adapter to gain access to first vial and a second end ending in second adapter to gain access to second vial; wherein the first adapters and the second adapter are joined together in vertical direction by means of horizontal wall; wherein the adapter connected to the vials by means of the ends.

15 Claims, 8 Drawing Sheets

(58) Field of Classification Search
USPC .......................................................... 604/413
See application file for complete search history.

(56) References Cited

U.S. PATENT DOCUMENTS

| | | | |
|---|---|---|---|
| 4,607,671 A | | 8/1986 | Aalto et al. |
| 4,759,756 A | * | 7/1988 | Forman ................. A61J 1/2089 604/413 |
| 4,847,366 A | | 7/1989 | Yamamoto et al. |
| 5,049,129 A | | 9/1991 | Zdeb et al. |
| 5,074,844 A | | 12/1991 | Zdeb et al. |
| 5,358,236 A | | 10/1994 | Maass et al. |
| 5,397,303 A | | 3/1995 | Sancoff et al. |
| 5,445,631 A | * | 8/1995 | Uchida ................. A61J 1/2089 604/412 |
| 5,743,312 A | | 4/1998 | Pfeifer et al. |
| 6,022,339 A | | 2/2000 | Fowles et al. |
| 6,113,583 A | | 9/2000 | Fowles et al. |
| 6,224,573 B1 | | 5/2001 | Yeager et al. |
| 6,238,372 B1 | | 5/2001 | Zinger et al. |
| 6,610,040 B1 | | 8/2003 | Fowles et al. |
| 6,948,522 B2 | * | 9/2005 | Newbrough .......... A61J 1/2089 137/550 |
| 7,294,122 B2 | * | 11/2007 | Kubo .................... A61J 1/2089 604/410 |
| 8,702,675 B2 | | 4/2014 | Imai |
| 10,426,702 B2 | * | 10/2019 | Henninger ............ A61J 1/2089 |
| 2002/0087141 A1 | * | 7/2002 | Zinger .................. A61J 1/2037 604/414 |
| 2012/0323210 A1 | * | 12/2012 | Lev ....................... A61J 1/2096 604/405 |
| 2020/0146937 A1 | * | 5/2020 | Naygauz ................ A61J 1/145 |

FOREIGN PATENT DOCUMENTS

| | | |
|---|---|---|
| WO | 02/062288 A1 | 8/2002 |
| WO | 03/082398 A2 | 10/2003 |

OTHER PUBLICATIONS

Sep. 10, 2019 International Preliminary Report on Patentability issued in International Patent Application No. PCT/IN2018/050115.
Thirumurthy Velpandian et al. "Extemporaneously Used Drug Formulations for Ocular Emergencies". Pharmacology of Ocular Therapeutics, 2016, Switzerland, pp. 385-418.

* cited by examiner

DEVICE, METHOD AND KIT FOR THE RECONSTITUTION OF A SOLID OR SEMI SOLID PHARMACEUTICAL COMPOSITION

FIELD OF INVENTION

The present invention generally relates to a novel device, method and kit for reconstitution of pharmaceutical composition. In particular it pertains to a novel device, method and kit meant for reconstitution of solid or semi solid pharmaceutical composition.

BACKGROUND OF THE INVENTION

Active pharmaceutical ingredients (APIs) meant for human or animal use are made as a complete formulations such as solutions, emulsions, suspensions, injections and drops meant for topical and body cavities etc. However, due to chemical/biological instability with solvents and procedures, many of them are not capable of use for appropriate situations. In such formulations, the powers and solvents are packed separately and solvents are injected with the help of syringes manually by the user during the time of its administration. This process requires skills and appropriate techniques to prevent contamination, variation in the reconstitution volume. Hence, the major disadvantage is that there are a number of variables between the original formational if the reconstitution techniques are inadequate.

Moreover, certain fortified drug formulations required for specific requirements are compromised due to the lack of easy and effective method for preparation for its instant and minimum defined period.

Certain drugs are preferably provided in powder or dry form (such as a lyophilized form), and require reconstitution prior to administration. Lyophilized drugs, for example, typically are supplied in a freeze-dried form that needs to be mixed with diluents to reconstitute the substance into a form that is suitable for injection.

Further, many pharmaceutical compositions are not capable of being stored for extended periods of time since their potency may change or due to their chemical instability. In order to overcome this problem of a short shelf life, such pharmaceutical products are stored as a solid component and a liquid component. Prior to use, the two components must be mixed together.

Due to this unavoidable physical, chemical and biological stability issues for many of the pharmaceutical ingredients required to be extemporaneously been dispensed time to time in liquid form by a qualified persons like pharmacists, nurses, physicians using sterile techniques like laminar flow bench during the time of eye emergencies (Velpandian et al). Lack of such facilities emergencies in remote places were such emergencies led to severe eye/ear/nose problems. Lack of sterile compounding pharmacies, emergency use of pharmaceutical sterile powers into pharmaceutical liquid for their installation into body cavities such as eye, nose, mouth, ear, are the major limitations.

Shelf life of oral vaccines is majorly limited due to stabilities issues in a reconstituted liquid state. In these conditions, maintaining cold chain for their preservation is a challenge which can compromise its efficacy over the period of time.

There are a number of devices and methods for drug reconstitution. The most common method is to inject a diluent contained in a syringe into a vial containing a dry component of the drug. After shaking the vial to mix the dry and liquid components, the user withdraws the reconstituted drug fluid from the vial using a second syringe. The second syringe is then used to inject the reconstituted drug to a patient. This reconstitution process is labour intensive and introduces numerous opportunities for contamination of the needle tip or vial contents. In addition, there is also a danger that the patient or practitioner will accidently be pricked by the exposed needle. These steps are even more intimidating for a patient attempting to self-inject a reconstituted drug for the first time. Further, the needle of the injection syringe may be dulled by insertion through the vial stopper. A dulled needle is more likely to be painful and/or cause scarring when later inserted into a patient.

Velpandian T and Das UK. Extemporaneously used drug formulations for ocular emergencies. 2016, (In) Pharmacology of Ocular Therapeutics (Ed) Velpandian, Springer, Switzerland, P. 385.

Many reconstitution or transfer devices are disclosed in U.S. Pat. Nos. 4,607,671, 4,847,366, 5,049,129, 5,074,844, 5,358,236, 5,743,312, 6,022,339, 6,113,583, 6,238,372, 6,224,573, 6,610,040 and PCT publications Ser. Nos. 99/27, 886, 01/68,166, 02/062,288 and 03/082,398.

Most of the devices disclosed in above mentioned patents and publications are too bulky, difficult to handle, complex, viable for contamination, too expensive and requires medical professional to operate.

In view of the deficiencies of current methods and devices for drug reconstitution, there is a need for a simpler device for reconstituting a pharmaceutical composition which enable the conversion of powered/lyophilized substances for their conversion into appropriate delivery methods such as instillation, or converting them into sprays or injections using suitable adopters.

This device reduces opportunities for user error by preventing exposure of needles before, during, and after use.

OBJECTIVE OF THE INVENTION

An object of the present invention is to provide a novel device, method and kit for reconstitution of solid or semi-solid pharmaceutical composition.

SUMMARY OF THE INVENTION

The present invention provides a novel device (100) for reconstitution of a solid or semi-solid pharmaceutical composition by a negative pressure differential comprises:
  (i) a first adapter (101) comprising a first connector (114), a first peripheral wall (103) wherein the first adapter (101) is coupled to the first vial (10) by means of a first connector (114);
  (ii) a second adapter (102) comprising a second connector (118), a second peripheral wall (104) wherein the second adapter (102) is coupled to the second vial (20) by means of a second connector (118);
  (iii) a transfer port (105) wherein the transfer port comprises a first end (112) ending in first adapter (101) to gain access to first vial (10) and a second end (116) ending in second adapter (102) to gain access to second vial (20);
  Wherein the first adapters (101) and the second adapter (102) are joined together in vertical direction by means of horizontal wall (150);
  Wherein the adapter (101, 102) connected to the vials (10, 20) by means of the ends (112, 116).

The present invention also provides a method for reconstitution of pharmaceutical composition using the device (100) as claimed in claim comprising the steps of:

(i) inserting the first vial (10) into the first adapter (101) and the second vial (20) into the second adapter (102) by means of the connectors (114, 118);

(ii) transferring the fluid present in the first vial (10) to second vial (20) by means of the transfer device (105) through piercing of the upper part (120) of the vial (10) and the upper part (140) of the second vial (20) wherein a positive pressure difference is created in the first vial (10) and a negative pressure difference is created in the second vial (20) to force material transfer between two vials (10, 20).

(iii) removing the vial (20) from the second adapter (102) and closing the vial (20) with lid (30)

Wherein the flow rate between first vial (10) and second vial (20) is automatically adjusted from initial high flow rate to one or more stepped-down lower flow rate with respect to uniform pressure difference to increase the pharmaceutical composition dissolution in second vial (20).

Further, the present invention also provides a kit for the reconstitution of pharmaceutical composition comprising:

(i) a reconstitution device (100) as claimed in claim 1;

(ii) a first vial (10) having an upper part (120) containing a solid or semi solid pharmaceutical composition;

(iii) a second vial (10) having an upper part (140) containing a liquid to obtain the reconstituted pharmaceutical composition;

(iv) optionally, a lid (30).

BRIEF DESCRIPTION OF FIGURES

FIGS. 1A, 1B and 1C depicts the perspective view of transfer device (100) (Trans ReCon™).

FIG. 3 depicts the perspective view of attached first vial (10), second vial (20), with transfer device (100).

FIG. 4 depicts the cross sectional of attached first vial (10), second vial (20), with transfer device (100) having adapter in conical shape.

FIG. 5 depicts perspective view of the single needle (106) having the ends (112, 116) and the ends (113,117)

FIG. 8 depicts the cross sectional view of attached first vial (10), second vial (20), with transfer device (100) having only one adapter inserted into a round segment (170).

DETAIL DESCRIPTION OF THE INVENTION

The present invention provides a novel device (100) for reconstitution of a solid or semi-solid pharmaceutical composition by a negative pressure differential comprises:

(i) a first adapter (101) comprising a first connector (114), a first peripheral wall (103) wherein the first adapter (101) is coupled to the first vial (10) by means of a first connector (114);

(ii) a second adapter (102) comprising a second connector (118), a second peripheral wall (104) wherein the second adapter (102) is coupled to the second vial (20) by means of a second connector (118);

(iii) a transfer port (105) wherein the transfer port comprises a first end (112) ending in first adapter (101) to gain access to first vial (10) and a second end (116) ending in second adapter (102) to gain access to second vial (20);

Wherein the first adapters (101) and the second adapter (102) are joined together in vertical direction by means of horizontal wall (150);

Wherein the adapter (101, 102) connected to the vials (10, 20) by means of the ends (112, 116).

The transfer device (100) may constructed of suitable material selected from the group comprising of glass, crystal, epoxy resin, acrylate polymer, polyethylene terephthalate (PET or PETE), polycarbonate, high-density polyethylene (HPPE), Polyvinyl chloride (PVC), Low-density polyethylene (LPDE), Polypropylene (PP), Polycarbonate, Polystyrene (PS), Silicon, polylactide or mixed polymers, polyvinylidine polymer, polyamide, methacrylate, matrix of zinc phosphate, silico phosphate, zinc polycaboxylate, glass ionomer, zinc oxide-eugenol, preferably polypropylene The transfer port (105) may be constructed of non reactive metal selected from the group comprising titanium, nickel, stainless steel, copper, gold, silver, iron, tin, zinc or their alloys which is coated or uncoated with non reactive materials selected from the group comprising silica, polymers, etc. or non reactive material such as ceramic, carbon fibre, silicon, monomer or polymer selected from the group comprising of polyethylene terephthalate (PET or PETE), polycarbonate, high-density polyethylene (HPPE), Polyvinyl chloride (PVC), Low-density polyethylene (LPDE), Polypropylene (PP), Polycarbonate, Polystyrene (PS) and Silicon, polylactide or mixed polymers, polyvinylidine polymer, polyamide, methacrylate, matrix of zinc phosphate, silico phosphate, zinc polycaboxylate, glass ionomer, zinc oxide-eugenol, preferably high density polyethylene, polylactide.

The ends (112, 116) of the transfer port (105) may be made of polypropylene tip on both side of mould, non reactive material such as ceramic, carbon fibre, silicon etc. Trans ReCon in which needle can be replaced by the polypropylene or polycarbonate tip on both sides by a single mould where the needle made up of the same or different material from any one of the monomer/polymer such as Polyethylene terephthalate (PET or PETE), polycarbonate, High-density polyethylene (HDPE), Polyvinyl chloride (PVC), Low-density polyethylene (LDPE), Polypropylene (PP), Polycarbonate, Polystyrene (PS) and Silicon etc, preferably high density polyethylene.

The adapters (101, 102) may be connected in vertical direction by means of screw, plug forming a horizontal wall (150) and the peripheral walls (103, 104) of the adapter (101, 102) may be in the shape of cone, square, rectangular, round such that the adapter may be hold in hand or by a clamping stand.

The first vial (10) may be calibrated with level of amount of volume from top end to accurately transfer volumes of fluid from first vial (10) to second vial (20).

The transfer device used for reconstitution (100) is disclosed in FIGS. 1A, 1B, 1C and 2 suitable for mixing contents of first vial (10, donor) with second vial (20, acceptor). The first vial (10) contains liquids for mixing with second vial (20) that contains solid or semi-solid pharmaceutical composition.

First adapter (101) comprises of the transfer port (105) to gain access to first vial (10) through piercing the upper part (120) of vial (10). The transfer port (105) consists of first end (112). The first end (112) of the transfer port is surrounded by the peripheral walls (103) which extend longitudinally from the first end of main body into the first adapter (101)

receivable portion. The first end (112) protrudes into the upper part (120) of first vial (10). The Adapter (101) further comprises first connector (114) in upper part of the adapter.

The vial (10) may be connected to adapter (101) by means of first connector (114) by screwing or locking or clamping.

Second adapter (102) comprises of the transfer port (105) to gain access to second vial (20) through piercing the upper part (140) of second vial (20). The transfer port (105) consists of second end (116). The second end (116) of the transfer port is surrounded by the peripheral walls (104) which extend longitudinally from the second end of main body into the second adapter (102) receivable portion. The second end (116) protrudes into the upper part (140) of second vial (10). The Adapter (102) further comprises second connector (118) in upper part of the adapter.

The vial (20) may be connected to adapter (104) by means of second connector (118) by screwing or locking or clamping.

Further, the transfer port (105) may comprises a single needle (106) or cannulas as shown in FIG. 5 comprises of two ends (112, 116) to gain access to first vial (10) and the ends (113, 117) to gain access to second vial (20) for transfer of fluid from first vial (10) to second vial (20). The needle (105) is long enough such that when the vials (10, 20) are secured in the 1 connectors (114, 118) of adapter (101, 102), the ends (112,116) have completely pierced the parts (120, 140) of the vials (10, 20). The transfer port (105) provides a passage way for the transfer of liquid between vial (10) and vial (20) through the lumen formed between two needles joint together in vertical direction forming a connector. The internal lumen diameter may be in range of 0.1-to 5 mm preferably 1.5 mm.

Figure 6:
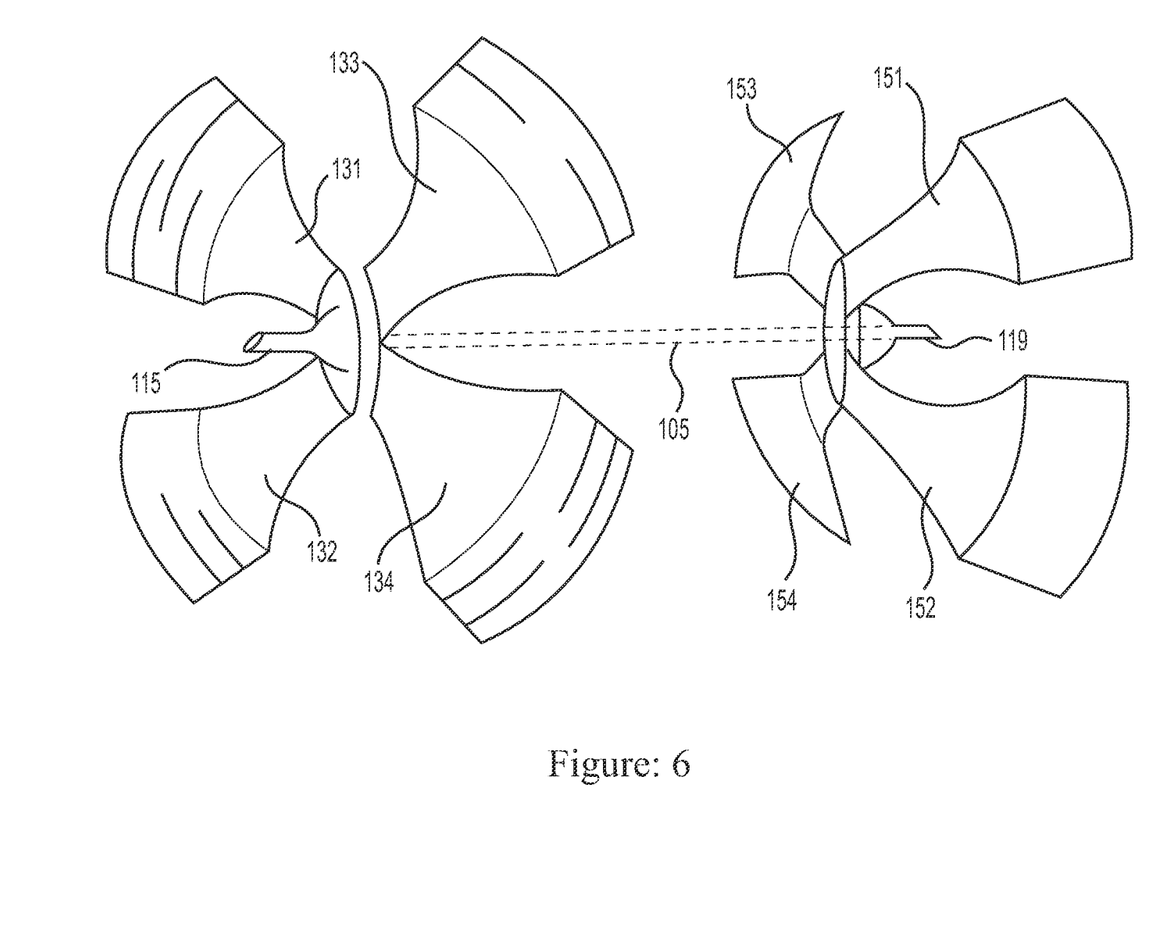
FIG. 6 depicts perspective view of cloverleaf configuration having four leafs to hold the needles of the transfer port (105).

Further, as disclosed in FIG. 6, the transfer port (105) comprises a needle (107) with ends (115, 119) surrounded by the cloverleaf configuration (130) having arms (131, 132, 133, 134) and the cloverleaf configuration (150) having arms (151, 152, 153, 154) at the joining of the adapters (101, 102) to transfer of fluid from first vial (10) to second vial (20).

Figure 7:
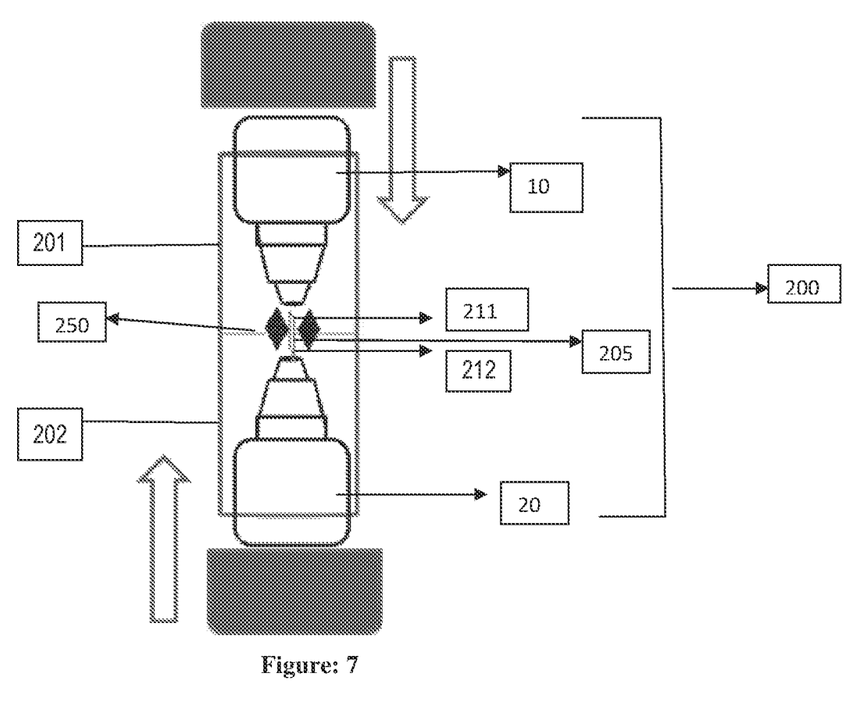
FIG. 7 depicts the cross sectional view of attached first vial (10), second vial (20), with transfer device (100) having adapter in rectangular shape.

In another embodiment as shown in FIG. 7, the present invention also discloses a device (100) for reconstitution of a solid or semi-solid pharmaceutical composition by comprises:
(i) a tube (200) having first chamber (201) and second chamber (202),
(ii) a transfer port (205) wherein the transfer port comprises a first end (211) ending in first chamber (201) to gain access to first vial (10) and a second end (212) ending in second chamber (202) to gain access to second vial (20),
Wherein the first chamber (201) and the second chamber (102) are separated by means of horizontal wall (250);
Wherein the chambers (201, 202) connected to the vials (10, 20) by means of the ends (211,212).

Figure 2:
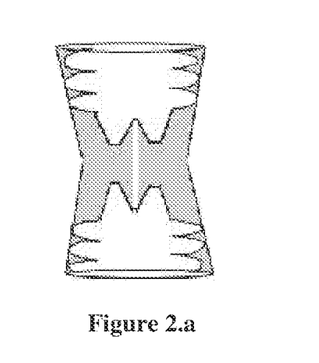
FIG. 2 depicts the cross sectional view of transfer device (100) (Trans ReCon™).

In one embodiment as shown in FIG. 2, the present invention also discloses a device (300) for reconstitution of a solid or semi-solid pharmaceutical composition comprises:
(i) a first adapter (301) comprising a first connector (314), a first peripheral wall (303) wherein the first adapter (301) is coupled to the first vial (10) by means of a first connector (314);
(ii) a transfer port (305) wherein the transfer port comprises a first end (312) ending in first adapter (301) to gain access to first vial (10) and a second end (316) without any adapter to gain access to second vial (20);
(iii) a segment device (170)

Wherein the first adapters (301) and transfer port (305) are fitted in centre of the segment device (370) in vertical direction by means of horizontal wall (350);
Wherein the adapter (301) connected to the vials (10) by means of the end (312) of the transport needle and the end (316) without any adapter is connected to second vial (20).

In another aspect, the present invention provides a method of reconstitution of pharmaceutical composition using the device (100) as claimed in claim comprising the steps of:
(i) inserting the first vial (10) into the first adapter (101) and the second vial (20) into the second adapter (102) by means of the connectors (114, 118);
(ii) transferring the fluid present in the first vial (10) to second vial (20) by means of the transfer device (105) through piercing of the upper part (120) of the vial (10) and the upper part (140) of the second vial (20) wherein a positive pressure differential is created in the first vial (10) and a negative pressure differential is created in the second vial (20) to force material transfer between two vials (10, 20).
(iii) removing the vial (20) from the second adapter (102) and closing the vial (20) with lid (30)

Wherein the flow rate between first vial (10) and second vial (20) is automatically adjusted from initial high flow rate to one or more stepped-down lower flow rate with respect to uniform pressure difference to increase the pharmaceutical composition dissolution in second vial (20).

In using the transfer device (105), adapters (101) and (102) are interconnected as shown in FIG. 3 and FIG. 4. The device comprises adapters (101, 102) are mated with vials (10, 20) as shown in FIGS. 3 and 4. The first end (112) protrudes in upper portion of first vial and pierces the seal of first vial (10), the diluents will automatically be drawn to second vial (20) through the lumen formed by transfer port (105). A negative pressure differential created in the second vial (20) and a positive pressure differential is created in the first vial (20) to force material transfer between the two vials which lead to formation of a pressure differential between a first vial (10) and a second vial (200), thereby enabling efficient material transfer between vials (10, 20).

The user may apply pressure externally in second vial (20) to balance difference between pressures or equalize the pressure difference for efficient flow rate. The pressure difference may be in range of 0.2-to 6 psi preferably 2 psi.

Alternatively, one vial may be kept at vacuum and another one may be kept under positive pressure to avoid human intervention to push the liquid into another vial while using the TransReCon™.

The flow rate between first vial (10) and second vial (20) is automatically adjusted from initial high rate to one or more stepped-down lower flow rates with respect to pressure difference and provide precise and variable flow rate that will increase dissolution of drug composition in second vial. The flow may be in range of 10 to 500 ml/hr, preferably 60 ml/hr (1 ml/mt)

The fluid is intermixed with pharmaceutical composition comprising powdered/concentrated/lyophilized ophthalmic composition contained in second vial (20). Once the solid/semi solid medicament and fluid are mixed thoroughly, vial (20) is removed from the adapter through unscrewing or unclamping or withdrawing. The fluid is intermixed with the pharmaceutical composition in second vial (20) is closed by lid (30) through screwing or clamping or locking and delivering the resulting mixture aseptically to a delivery device.

In another aspect, the present invention also provides a kit for the reconstitution of pharmaceutical composition comprising:
(i) a reconstitution device (100) as claimed in claim 1;
(ii) a first vial (10) having an upper part (120) containing a solid or semi solid pharmaceutical composition;
(iii) a second vial (10) having an upper part (140) containing a liquid to obtain the reconstituted pharmaceutical composition;
(iv) optionally, a lid (30).

Without being limited by theory, it is submitted that the present invention provide a method for reconstitution of pharmaceutical ophthalmic composition using transfer device. The present invention provides a novel transfer device comprising adapters that are used to secure vials containing solid or liquid substance thereby avoiding needle stick injuries to operators, makes process simple for efficient transfer and mixing. The present device provides uniform pressure difference and flow rate for efficient transfer between two vials. The present invention provides a transfer device which is economical, easy to carry, maintain sterile environment throughout the transfer and prevents contamination in the reconstituted pharmaceutical composition for ophthalmic use.

Advantages

The various advantages of the transfer device of the present invention include:
1. This invention enables, fresh reconstitution of drugs for their use especially drugs having low self life.
2. The present device eliminates needle stick injuries during reconstitution when a hypodermic needle is used by a non-professional.
2. The present device is easy to operate, carry and transfer diluents aseptically from one vial to another in an aseptic manner.
3. The present invention provides uniform flow rate for efficient mixing and transfer of diluents from one vial to another by the patient or his/her attendant.
4. The present device is economical and does not require medical/paramedical professional for its usage can be used at places where sterile dispensing facility is unavailable.
5. It avoids the requirement of locking mechanism in the eye drop vials which are reported to fall while using the eye drop.
6. Drugs having shorter shelf-life in aqueous solutions can use administered using this device at emergencies.
7. Lyophilised biologicals can be reconstituted using this device for instillation in to eye, nose, ear and/or other body cavities
8. Preservative free drugs can be reconstituted for shorter duration of application.
9. Drugs can be safely taken to space stations for reconstitution and application into body cavities.
10. Nanoparticle based formulations can be administered through this device.
12. Vaccines can be transported to remote locations in dry form (with higher stability) without the cold chain requirement and can be reconstituted prior to administration.
13. After enabling the reconstitution of pharmaceutical compositions using this device the resultant composition in liquid form can be administered as instillations, spary, injectables, Roll ons, by replacing the suitable cap variables.

It may be understood by a person skilled in the art that the present invention is accompanied by figures. The figures form a part of the invention. The figures encompass the embodiment as illustrated in each figure. It is understood by a person skilled in the art that other variations of the transfer device and combinations thereof are envisaged within the scope of the invention. It is understood by a person skilled in the art that other variations of the transfer device and combinations thereof are envisaged within the scope of the invention.

We claim:

1. A novel device for reconstitution of a solid or semi-solid pharmaceutical composition by a negative pressure differential comprises:
(i) a first adapter comprising a first connector, a first peripheral wall wherein the first adapter is coupled to a first vial by means of the first connector;
(ii) a second adapter comprising a second connector, a second peripheral wall wherein the second adapter is coupled to a second vial by means of the second connector; and
(iii) a transfer port wherein the transfer port comprises only one single needle with only one channel, the single needle having a first end ending in the first adapter to gain access to the first vial and a second end ending in the second adapter to gain access to the second vial, wherein:
the first adapter and the second adapter are joined together in vertical direction by means of a horizontal wall;
the first adapter and the second adapter are connected to the first vial and the second vial by means of the first end and the second end;
the first end of the single needle is surrounded by a first cloverleaf configuration having arms and the second end of the single needle is surrounded by a second cloverleaf configuration having arms in order to hold the single needle at a joining of the first adapter and the second adapter in order to transfer fluid from the first vial to the second vial; and
the first cloverleaf configuration and the second cloverleaf configuration are located within the first adapter and the second adapter, respectively.

2. The device as claimed in claim 1, wherein the device is constructed of material selected from the group comprising of glass, crystal, epoxy resin, acrylate polymer, polyethylene terephthalate (PET or PETE), polycarbonate, high-density polyethylene (HPPE), Polyvinyl chloride (PVC), Low-density polyethylene (LPDE), Polypropylene (PP), Polycarbonate, Polystyrene (PS) and Silicon.

3. The device as claimed in claim 1, wherein the transfer port is constructed of non reactive metal selected from the group comprising iron, nickel, stainless steel, copper, gold, silver, iron, tin, zinc or their alloys which is coated or uncoated with non reactive materials selected from the group comprising silica, polymers etc.

4. The device as claimed in claim 1, wherein the transfer port is made of non reactive material including ceramic, carbon fibre, silicon, monomer or polymer selected from the group comprising of polyethylene terephthalate (PET or PETE), polycarbonate, high-density polyethylene (HPPE), Polyvinyl chloride (PVC), Low-density polyethylene (LPDE), Polypropylene (PP), Polycarbonate, Polystyrene (PS) and Silicon.

5. The device as claimed in claim 1, wherein the ends of the transfer port are made of polypropylene or non reactive material including ceramic, carbon fibre and silicon.

6. The device as claimed in claim 1, wherein the peripheral walls of the first adapter and the second adapter are in the shape of cone, square, rectangular, or round.

7. The device as claimed in claim 1, wherein the connectors of the first adapter and the second adapter are selected from the group comprising screw ring, lock ring, and clamp ring.

8. The device as claimed in claim 1, wherein the first adapter and the second adapter are connected by means of a screw, or a plug.

9. The device as claimed in claim 1, wherein the first end and the second end of the transfer port are a pointed end, or a blunt end.

10. A method of reconstitution of pharmaceutical composition using the device as claimed in claim 1 comprising the steps of:
 (i) inserting the first vial into the first adapter and the second vial into the second adapter by means of the connectors;
 (ii) transferring the fluid present in the first vial to second vial by means of the transfer port through piercing of an upper part of the first vial and an upper part of the second vial wherein a positive pressure in the first vial and a negative pressure in the second vial to force the fluid transfer between the first and the second vial; and
 (iii) removing the second vial from the second adapter and closing the second vial with a lid;
 wherein a flow rate between the first vial and second vial is automatically adjusted from initial high flow rate to one or more stepped-down lower flow rate with respect to uniform pressure difference to increase the pharmaceutical composition dissolution in the second vial.

11. The method as claimed in claim 10, wherein the device is sterilized by a chemical process using ethylene oxide, a physical process using hot-water, an autoclave or an irradiative process using electron-beam or gamma processes.

12. The method as claimed in claim 10, wherein a flow rate is in the range of 10 to 500 ml/hr.

13. The method as claimed in claim 10, wherein a pressure difference between the first and second vial is in a range of 0.2-to 6 psi.

14. The method as claimed in claim 10, wherein the second vial is kept under vacuum and the first vial is kept under positive pressure to avoid human intervention to push the fluid from the first vial into the second vial.

15. A kit for the reconstitution of pharmaceutical composition comprising:
 (i) a reconstitution device as claimed in claim 1;
 (ii) the first vial having an upper part containing a solid or semi solid pharmaceutical composition; and
 (iii) the second vial having an upper part containing a liquid to obtain the reconstituted pharmaceutical composition.

* * * * *